US011825821B2

(12) United States Patent
Cartier et al.

(10) Patent No.: US 11,825,821 B2
(45) Date of Patent: Nov. 28, 2023

(54) INSECT BREEDING APPARATUS AND METHODS

(71) Applicant: Solider Fly Technologies, Inc., Port Allen, LA (US)

(72) Inventors: Kristen Rebecca Cartier, Madera, CA (US); Robert Benjamin Runyon, Madera, CA (US)

(*) Notice: Subject to any disclaimer, the term of this patent is extended or adjusted under 35 U.S.C. 154(b) by 0 days.

(21) Appl. No.: 17/359,037

(22) Filed: Jun. 25, 2021

(65) Prior Publication Data
US 2021/0400935 A1 Dec. 30, 2021

Related U.S. Application Data

(60) Provisional application No. 63/044,108, filed on Jun. 25, 2020.

(51) Int. Cl.
A01K 67/033 (2006.01)

(52) U.S. Cl.
CPC .................. A01K 67/033 (2013.01)

(58) Field of Classification Search
CPC .................................................. A01K 67/033
See application file for complete search history.

(56) References Cited

U.S. PATENT DOCUMENTS

| 2,670,562 | A | * | 3/1954 | Gould | A01K 97/04 119/6.5 |
| 3,468,289 | A | * | 9/1969 | Daniel | B65D 81/266 119/6.5 |
| 3,939,883 | A | * | 2/1976 | Harrell | B65B 3/32 141/238 |
| 4,368,690 | A | * | 1/1983 | Tenzer | A01K 67/033 119/6.6 |
| 4,850,305 | A | * | 7/1989 | Georgi | A01K 67/033 119/303 |
| 5,074,247 | A | * | 12/1991 | Gupta | A01K 1/031 119/6.5 |
| 5,158,497 | A | * | 10/1992 | Rossignol | A01K 57/00 449/2 |
| 5,178,094 | A | * | 1/1993 | Carr | A01K 67/033 119/6.5 |
| 5,351,643 | A | * | 10/1994 | Hughes | A01K 67/033 119/6.5 |
| 6,244,213 | B1 | * | 6/2001 | Tedders | A01K 67/033 119/6.6 |
| 6,397,782 | B1 | * | 6/2002 | Cope | A01K 67/033 119/475 |

(Continued)

Primary Examiner — Monica L Perry
Assistant Examiner — Aaron M Rodziwicz
(74) Attorney, Agent, or Firm — Zachary Christiansen

(57) ABSTRACT

The invention is an apparatus which houses and facilitate insect breeding, including but not limited to the breeding of black soldier flies (*Hermetia Illucens*). Embodiments of the invention house insects before, during, and after the mating process. Insects are inserted into the invention usually in a pre-sexually mature state (e.g. the larvae, prepupae, or pupae state). After a period of time, the insects become sexually mature and are able to mate. After mating, the insects are attracted to lay eggs (oviposit) onto egg collection substrates within the invention. Embodiments of the invention allow for the insect eggs to be collected periodically, and/or allows for the insect eggs to hatch in which case the newly emerged insects (e.g. larvae) are retrieved as frequently as desired.

1 Claim, 8 Drawing Sheets

(56) References Cited

U.S. PATENT DOCUMENTS

| | | | | |
|---|---|---|---|---|
| 8,733,284 | B2* | 5/2014 | Courtright | A01K 29/00 |
| | | | | 119/6.6 |
| 9,462,795 | B2* | 10/2016 | Chin | A01K 67/033 |
| 9,510,572 | B2* | 12/2016 | Aldana | A01K 67/033 |
| 9,642,344 | B2* | 5/2017 | Unger | A01K 67/033 |
| 9,844,223 | B2* | 12/2017 | Vickerson | A01M 1/106 |
| 10,051,845 | B1* | 8/2018 | Massaro | A01K 29/005 |
| 10,159,229 | B2* | 12/2018 | Marchant | F21V 7/22 |
| 10,188,083 | B2* | 1/2019 | Leo | A01K 67/033 |
| 10,264,769 | B2* | 4/2019 | Leo | A23K 20/163 |
| 10,278,368 | B1* | 5/2019 | Peeters | A01K 1/031 |
| 10,667,502 | B2* | 6/2020 | Wu | A01K 67/033 |
| 10,842,138 | B1* | 11/2020 | Lolley | A01K 67/033 |
| 10,912,288 | B1* | 2/2021 | Hall | A01K 67/033 |
| 11,291,190 | B1* | 4/2022 | Peeters | A01K 67/033 |
| 2013/0319334 | A1* | 12/2013 | Newton | A01K 67/033 |
| | | | | 119/51.01 |
| 2014/0020630 | A1* | 1/2014 | Courtright | A01K 67/033 |
| | | | | 119/6.6 |
| 2016/0066552 | A1* | 3/2016 | Arsiwalla | A01K 1/0047 |
| | | | | 119/6.5 |
| 2018/0077912 | A1* | 3/2018 | Comparat | A01K 67/033 |
| 2018/0206473 | A1* | 7/2018 | Massaro | A01M 29/12 |
| 2019/0085279 | A1* | 3/2019 | Leo | A23L 2/56 |
| 2020/0229411 | A1* | 7/2020 | Leo | C12N 15/86 |
| 2020/0370073 | A1* | 11/2020 | Leo | C12N 1/12 |
| 2021/0137137 | A1* | 5/2021 | Leo | A23K 40/20 |

* cited by examiner

INSECT BREEDING APPARATUS AND METHODS

CROSS REFERENCE TO RELATED APPLICATIONS

This application claims the benefit of U.S. Provisional Application No. 63/044,108 filed Jun. 25, 2020.

REFERENCE TO GOVERNMENT FUNDING SOURCES

Not applicable.

REFERENCE TO SEQUENCE LISTING

Not applicable.

FIELDS OF THE INVENTION

The disclosure as detailed herein is in the technical field of an apparatus' for insect breeding. More specifically, the present disclosure relates to the technical field of breeding apparatus intended to house and facilitate insect breeding. Even more specifically, the present disclosure relates to the technical field of breeding apparatus for the breeding of black solder flies.

DESCRIPTION OF RELATED ART

A growing problem in the near future is finding a way to provide a sufficient amount of healthy protein to an expanding population. It is projected that by the year 2050, the world's population will increase from approximately 7 billion people to 9 billion people. "More than two-thirds of the world's agricultural land is already used to grow feed for livestock, yet world meat consumption is on track to double by 2050." Bourne, J. K. (2016). The end of plenty: The race to feed a crowded world. NY, NY: W. W. Norton & Company. Furthermore, rising incomes, higher standards of living, and urbanization are driving a global dietary transition in which traditional diets are replaced by diets higher in, among other nutrients, meats. As arable land, water, and feed sources become scarce, the world will be in urgent need of a solution to the "protein problem". The use of black soldier fly larvae as a protein source could effectively address this growing issue.

Protein production from insect larvae has enormous efficiency advantages relative to other methods. Compared to soy protein production, for example, black soldier fly insect protein can be more than 2,000 times more efficient in terms of protein production per acre of land required.

In the race to feed a crowded world with dwindling agricultural land, black soldier fly breeding and larvae rearing could be an effective solution to a once perplexing problem. With the demand for meat production expected to double in the coming decades, innovation in livestock feed to produce that meat is crucially important.

By producing and harvesting insects as feed supplements using optimized techniques, black soldier fly larvae rearing can help the feed industry rise to the challenge of effectively producing sustainable protein. The use of black soldier fly larvae could fortify the world's livestock by reducing agricultural waste, minimizing land use, and mitigating carbon emissions.

GENERAL SUMMARY OF THE INVENTION

The Breeding Module (101) contains Access Ports (603) that allow for items to be inserted and/or removed from the Breeding Module (101). These items include but are not limited to: live insects, oviposition attractants, egg collection substrates, insect eggs, dead insects, and liquid sources. The Access Ports (603) may change in size, shape, and quantity and may be located anywhere on the Breeding Module (101). The Breeding Module (101) is composed of materials that can be cleaned and/or sanitized for reuse (e.g. plastic or metal). The Breeding Module (101) contains at least one or more ports ("permeable ports") that include a permeable material covering an open section or void in the bottle and/or IBC frame of the Breeding Module (101). The permeable material can include but is not limited to a perforated, screened, and/or weaved material. The permeable ports allow for one or more of the following: visibility of the inside of the Breeding Module (101), natural and/or artificial light penetration into the Breeding Module (101), the equalization of the humidity, temperature, and air quality between the ambient conditions outside the Breeding Module (101) and the conditions inside the Breeding Module (101), adding substances into the module (e.g. liquid), as well as provide access for the insects to a liquid source. The liquid sources may include but are not limited to: a wet sponge or wet towel. The permeable ports are strategically placed such that the Breeding Module (101) can maintain a specific range of desired temperature and humidity values. The permeable ports may change in size, shape, and/or quantity and may be located anywhere on the Breeding Module (101). The Breeding Module (101) also contains cleaning and Drainage Ports (501) to allow for washing equipment to clean and/or sanitize, as well as drain contents (e.g. dead insects) from the Breeding Module (101) as often as desired.

DETAILED DESCRIPTION

Figure 1:
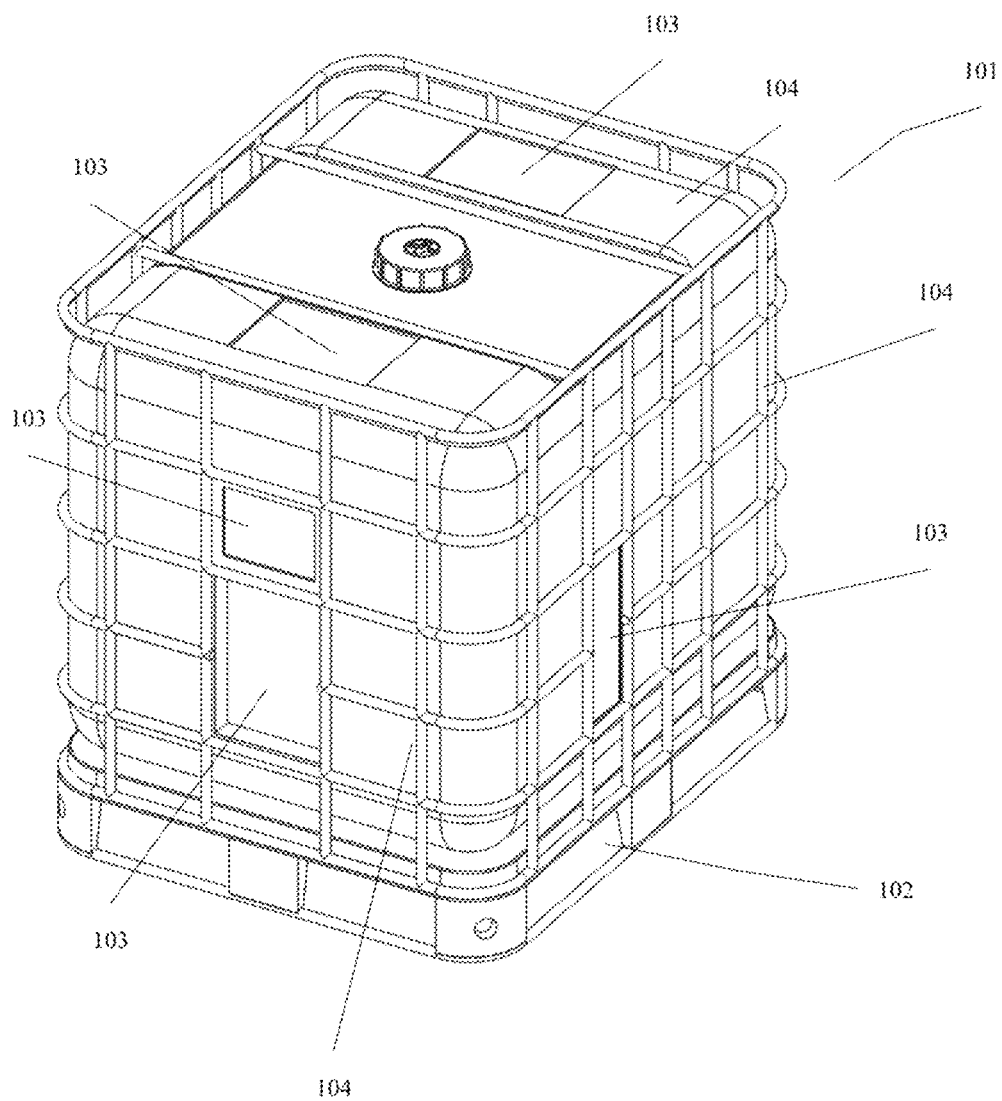
FIG. 1 which shows an Isometric View of the Insect Breeding Apparatus.

One or more different inventions may be described in the present application. Further, for one or more of the inventions described herein, numerous alternative embodiments may be described; it should be appreciated that these are presented for illustrative purposes only and are not limiting of the inventions contained herein or the claims presented herein in any way. One or more of the inventions may be widely applicable to numerous embodiments, as may be readily apparent from the disclosure. In general, embodiments are described in sufficient detail to enable those skilled in the art to practice one or more of the inventions, and it should be appreciated that other embodiments may be utilized and that structural, logical, software, electrical and other changes may be made without departing from the scope of the particular inventions. Accordingly, one skilled in the art will recognize that one or more of the inventions may be practiced with various modifications and alterations. Particular features of one or more of the inventions described herein may be described with reference to one or more particular embodiments or figures that form a part of the present disclosure, and in which are shown, by way of illustration, specific embodiments of one or more of the inventions. It should be appreciated, however, that such features are not limited to usage in the one or more particular embodiments or figures with reference to which they are described. The present disclosure is neither a literal description of all embodiments of one or more of the inventions nor a listing of features of one or more of the inventions that must be present in all embodiments.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an embodiment with several components in communication with each other does not imply that all such components are required. To the contrary, a variety of optional components may be described to illustrate a wide variety of possible embodiments of one or more of the inventions and to illustrate one or more aspects of the inventions more fully. Similarly, although process steps, method steps, algorithms or the like may be described in a sequential order, such processes, methods, and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the invention(s), and does not imply that the illustrated process is preferred. Also, steps are generally described once per embodiment, but this does not mean they must occur once, or that they may only occur once each time a process, method, or algorithm is carried out or executed. Some steps may be omitted in some embodiments or some occurrences, or some steps may be executed more than once in a given embodiment or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments of one or more of the inventions need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of embodiments of the present invention in which, for example, functions may be executed out of order from that shown or discussed, including substantially concurrently or in reverse order, depending on the functionality involved, as would be understood by those having ordinary skill in the art.

The Insect Breeding Apparatus comprises one or more Egg Collection Substrates, one or more Light Sources (401), one or more insects and a Breeding Module (101).

Referring now to FIG. 1, which shows an Isometric View of the Insect Breeding Apparatus.

The Breeding Module (101) comprises one or more Fluid Delivery Systems (402), one or more Walls (104), a Breeding Module Moving Enabler (102) and one or more Ports (103).

The breeding module may come in various shapes and sizes, and is composed of a material that can be washed out and sanitized for reuse (i.e. plastic). One example of a Breeding Module (101) can be created by modifying an intermediate bulk container. The breeding module may come in many shapes (i.e. cubic or rectangular). The Breeding Module (101) may have a fully or partially sloped surface that facilitates draining while the unit is in a desired configuration (i.e. upright).

The Breeding Module (101) is intended to house insects before, during, and after the mating process. First, insects are inserted into the Breeding Module (101) in the larvae or pupae state. The larvae or pupae will be inserted into the Breeding Module (101) using one of the methods below:

a) In individual containers that are added through an access port and placed on the floor of the Breeding Module (101).

b) Within individual containers that are added through an access port and placed on stands or shelves within the Breeding Module (101).

c) Inserted through a port (i.e. Access Port (603), Drainage Port (501), or Cleaning Port (202)) directly into a designated area contained within the breeding module, which may be built into the structure of the Breeding Module (101).

After a period of time, adult insects emerge and are allowed to mate. After the mating process is completed, the pregnant insects search for a place to deposit eggs (oviposit). The Breeding Module (101) may contain one or more egg collection substrates for attracting the oviposition and for the collection of eggs. The eggs deposited on the egg collection substrate may be collected using any of the methods listed below:

(a) Removing the substrates from the breeding module through an access port with eggs attached for later collection.

(b) Removing the eggs from the substrates while the substrate is still located within (or is still attached to) the breeding module, and retrieving the eggs from the Breeding Module (101) through an Access Port (603).

(c) Allowing the eggs to hatch such that with the newly emerged insects (i.e. larvae) collect in a specific location (i.e. container) within the breeding module for later extraction.

As used in the invention there are several types of Ports (103) which are contemplated A Drainage Port (501), a Cleaning Port (202), an Access Port (603), a Perforated Port (501) and a Fluid Delivery Port (602). The Ports (103) are apertures which are located on one or more of the Walls (104) of the Breeding Module (101).

The Walls (104) are the sides of the Breeding Module (101) that create an enclosed space of the Breeding Module (101). In a preferred embodiment of the invention the Walls (104) can be made of a material that can be sanitized and washed out for reuse an example of which is plastic. The material may be of any level of transparency.

The Breeding Module (101) moving enabler is a structure which provides Access Ports (603) for various machinery to interact with during the moving of the Breeding Module (101). One example of a Breeding Module (101) moving enabler is a pallet. In this version the Breeding Module (101) is able to be moved with a standard forklift or handcart. Furthermore, the Breeding Module (101) is able to be stored on standard pallet racking.

Figure 2:
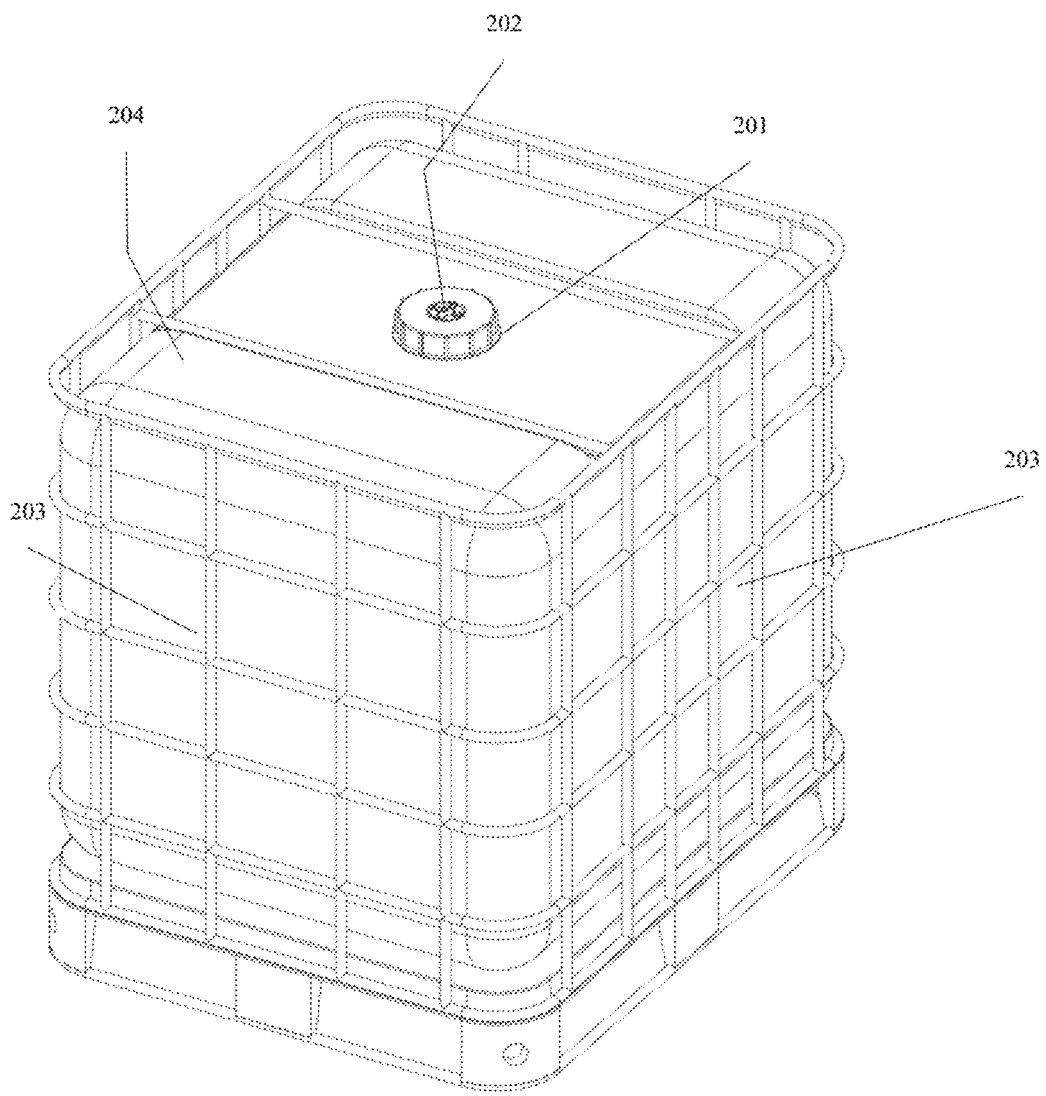
FIG. 2 which shows an additional Isometric View of the Insect Breeding Apparatus.

Referring now to FIG. 2, which shows an additional Isometric View of the Insect Breeding Apparatus.

The Cleaning Port (202) comprises a Cleaning Cap (201). The purpose of the Cleaning Port (202) is to allow for washing the inside of the Breeding Module (101) between uses.

The Cleaning Cap (201) allows for the aperture of the Cleaning Port (202) can be closed when the Breeding Module (101) is not being actively cleaned. In this manner the Breeding Module (101) can be closed off and the insects remain inside when the Cleaning Port (202) is not actively in use. The Cleaning Cap (201) stays installed on the cleaning port when the Breeding Module (101) is populated to ensure that no insects are able to leave the module.

The Side Wall (203) is a wall of the Breeding Module (101). It is positioned on an axis which is perpendicular to both the Lid (204) and the Breeding Module Moving Enabler (102).

The Lid (204) is a wall which is positioned on the top of the Breeding Module (101).

Figure 3:
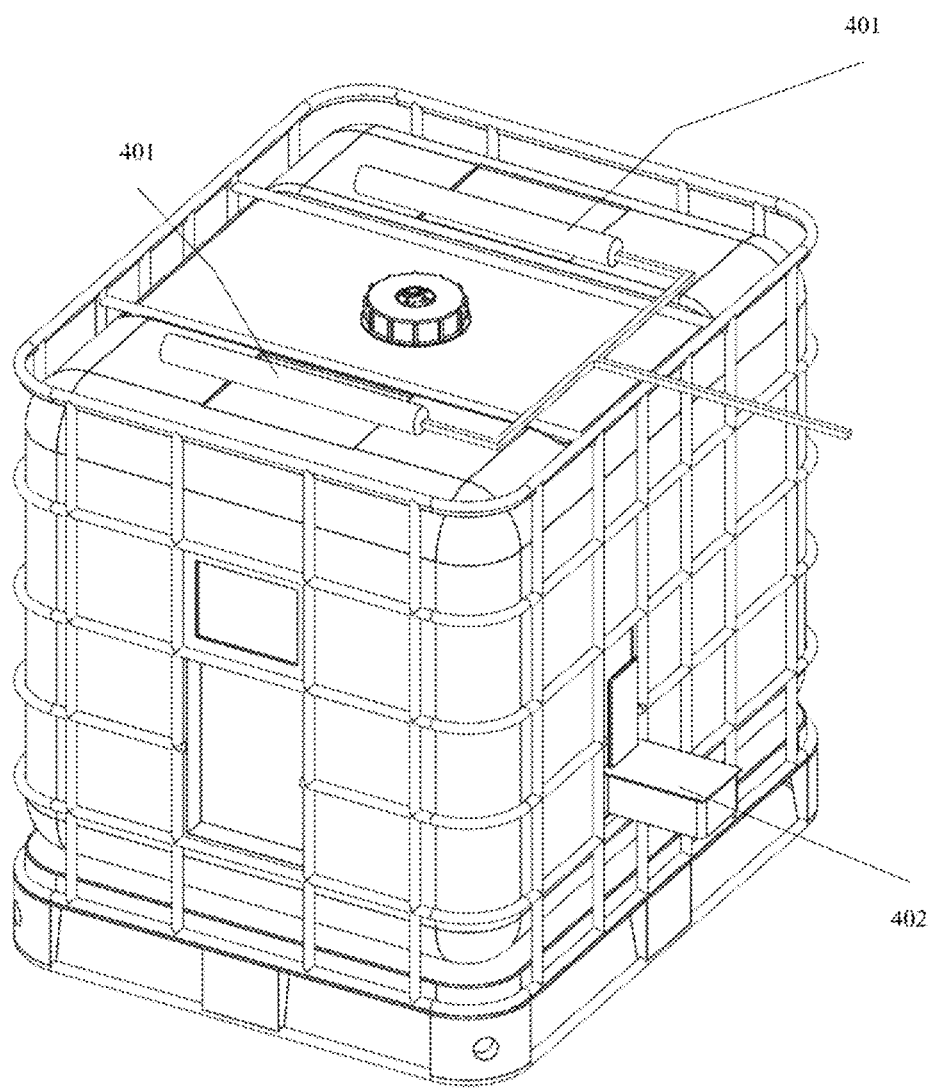
FIG. 3 which shows another Isometric View of the Insect Breeding Apparatus.

Referring now to FIG. 3, which shows another Isometric View of the Insect Breeding Apparatus.

The Light Source (401) is a device which is capable of emitting natural and/or artificial, and may consist of at least one wavelength of visible light and/or one wavelength of non-visible light. The Light Source (401) can be positioned in multiple locations. The purpose of the Light Source (401) is to provide one or more wavelengths of visible light and one or more wavelengths of non-visible light.

The Fluid Delivery System (402) comprises a Fluid Delivery System Lid (802), a Fluid, an Absorbent Material (801), and an Impermeable Container (901). The Delivery System may either be placed inside the breeding module, or on the outside of the breeding module providing insects access to the Absorbent Material (801) through a perforated surface or screen. One end of the Absorbent Material (801) being submerged into the liquid within the Impermeable Container (901), and one end exposed above the Fluid Delivery System Lid (802) to provide fluid (i.e. water) access to the insects. The Fluid Delivery System (402) may come in a variety of shapes, sizes, and configurations. The fluid level must remain below the level of the Fluid Delivery System Lid (802) at all times while the Fluid Delivery System (402) is within the breeding module. The insects will be able to land directly onto the Absorbent Material (801) to obtain fluid for consumption or bathing.

Figure 4:
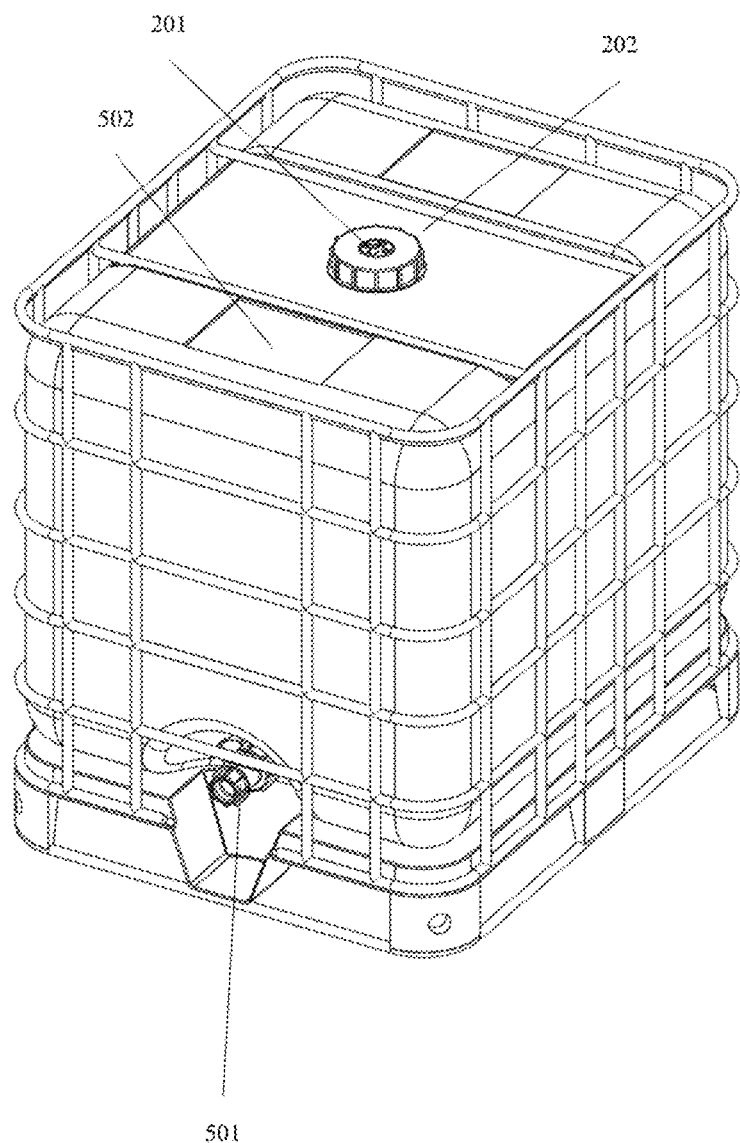
FIG. 4 which shows another Isometric View of the Insect Breeding Apparatus.

Referring now to FIG. 4, which shows another Isometric View of the Insect Breeding Apparatus.

The Drainage Port (501) allows for the cleaning solution to drain from the Breeding Module (101). The Drainage Port (501) can come in various shapes and sizes and may be located on one or more of the Walls (104) of the Breeding Module (101). The drainage port is intended to allow for liquid and debris (i.e. dead fly bodies) to exit the Breeding Module (101) during and after the cleaning process. The drainage port will remain closed while the breeding module is populated and in use to ensure that the insects remain within the module at all times.

Figure 5:
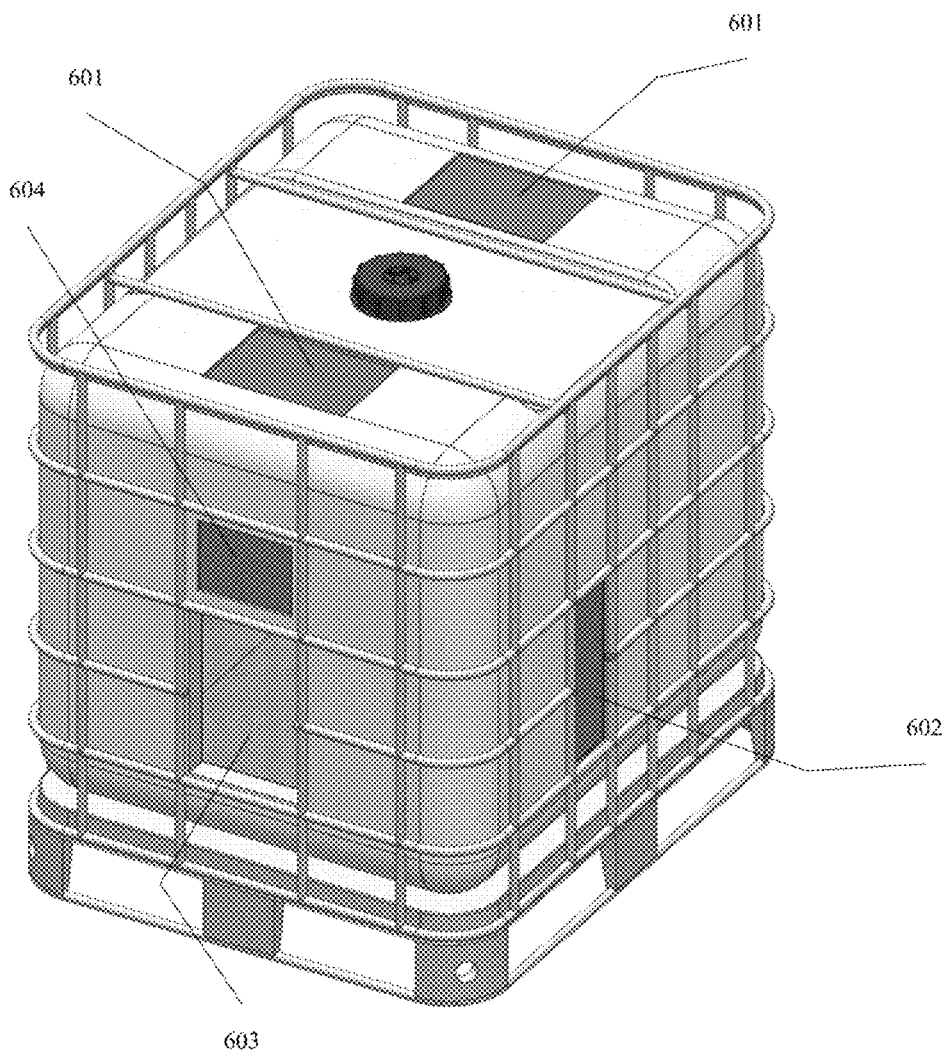
FIG. 5 which shows another Isometric View of the Insect Breeding Apparatus.

Referring now to FIG. 5, which shows another Isometric View of the Insect Breeding Apparatus.

The perorated port comprises a Screened Material (701). This Screened Material (701) is a material which has one or more apertures of varying sizes. This apertures permit certain things such as light, air or other fluids which are smaller than the perorations to pass through the Perforated Port (501) while inhibiting objects that are larger than size of the apertures on the Perforated Port (501). Any of the Perforated Ports (501) can be located on any one of the sides of the Breeding Module (101).

One purpose of the Perorated Port as used in the invention is to allow and permit light from the Light Source (401) to pass into the Breeding Module (101) while ensuring that the insects remain within the Breeding Module (101) at all times. Another purpose of the Perforated Port (501) is to provide a spot in which the contents on the inside of the Breeding Module (101) can be observed without having to open the Breeding Module (101) in this way the Perforated Port (501) acts as a Viewing Port (604).

When used as a ventilation port in the invention the Perforated Port (501) The screened or perforated material allows for air to pass through, while ensuring that the insects remain within the breeding module at all times. These ventilation ports may allow for the humidity, temperature, and air quality to equalize between the ambient conditions outside the module and the conditions inside the module.

Since the characteristics and requirements for the ventilation, light, and view ports are all similar, it is possible to combine the purposes of one or more Ports (103) to meet the requirements of multiple Ports (103) (i.e. put a light above a ventilation port making the port both the light port and the ventilation port). As a result, each breeding module may contain at least one perforated port that may be used as the ventilation port and/or light port, and/or view port.

The Viewing Port (604) is an aperture by which the inside of the Breeding Module (101) can be easily visualized while still containing the insects within the Breeding Module (101).

The aperture of the Fluid Delivery Port (602) is sized in such a manner to permit the Fluid Delivery System (402) to be inserted and removed from the Breeding Module (101). In this manner the Fluid Delivery System (402) can be inserted and removed from the Breeding Module (101) as needed for the continued maintenance of the Fluid Delivery System (402).

The Access Port (603) further comprises one or more doors. The Access Port (603) may be used for inserting and removing materials such as: eggs, egg laying substrates, larvae containers, and liquid sources. These Ports (103) may consist of mechanisms that ensure that the Access Port (603) is self-closing in such a way as to ensure that the insects are contained within the breeding module when the Ports (103)

are closed (ie. magnetic doors, sprung hinges). Each Breeding Module (101) may contain at least one Access Port (603). The Access Port (603) can be located at any place on the Walls (104) of the Breeding Module (101).

The door serves the purpose of allowing the aperture of the Access Port (603) to be opened and closed as needed to gain access through this aperture. When it is in the closed position the insects which are in the Breeding Module (101) remain in the Breeding Module (101). When the door is in the open position it allows access to the inside of the Breeding Module (101) from the outside.

Figure 6:
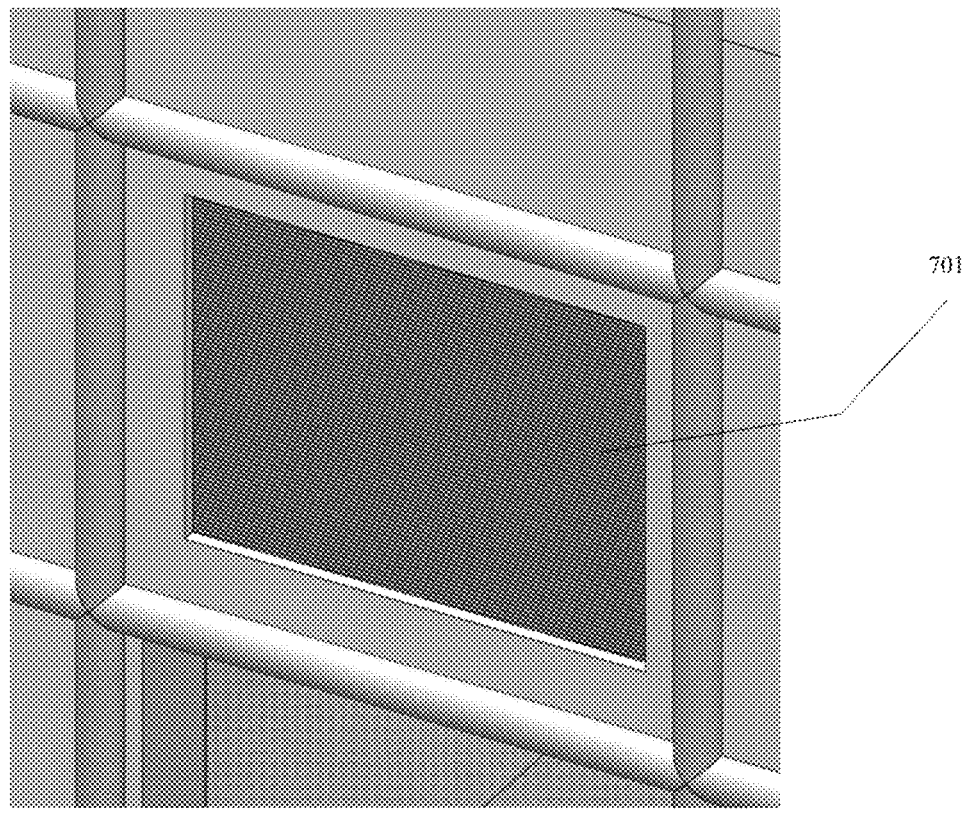
FIG. 6 which shows an exploded and upclose view of the Screened Material (701).

Referring now to FIG. 6, which shows an exploded and upclose view of the Screened Material (701).

The Screened Material (701) is a material which is capable of allowing certain particles to enter the space of the Breeding Module (101) which are below a threshold of the size of the screen. In one embodiment of the invention the Screened Material (701) is sized such that light and air are permitted to enter the Breeding Module (101) but that the insects are not permitted to leave the module.

Figure 7:
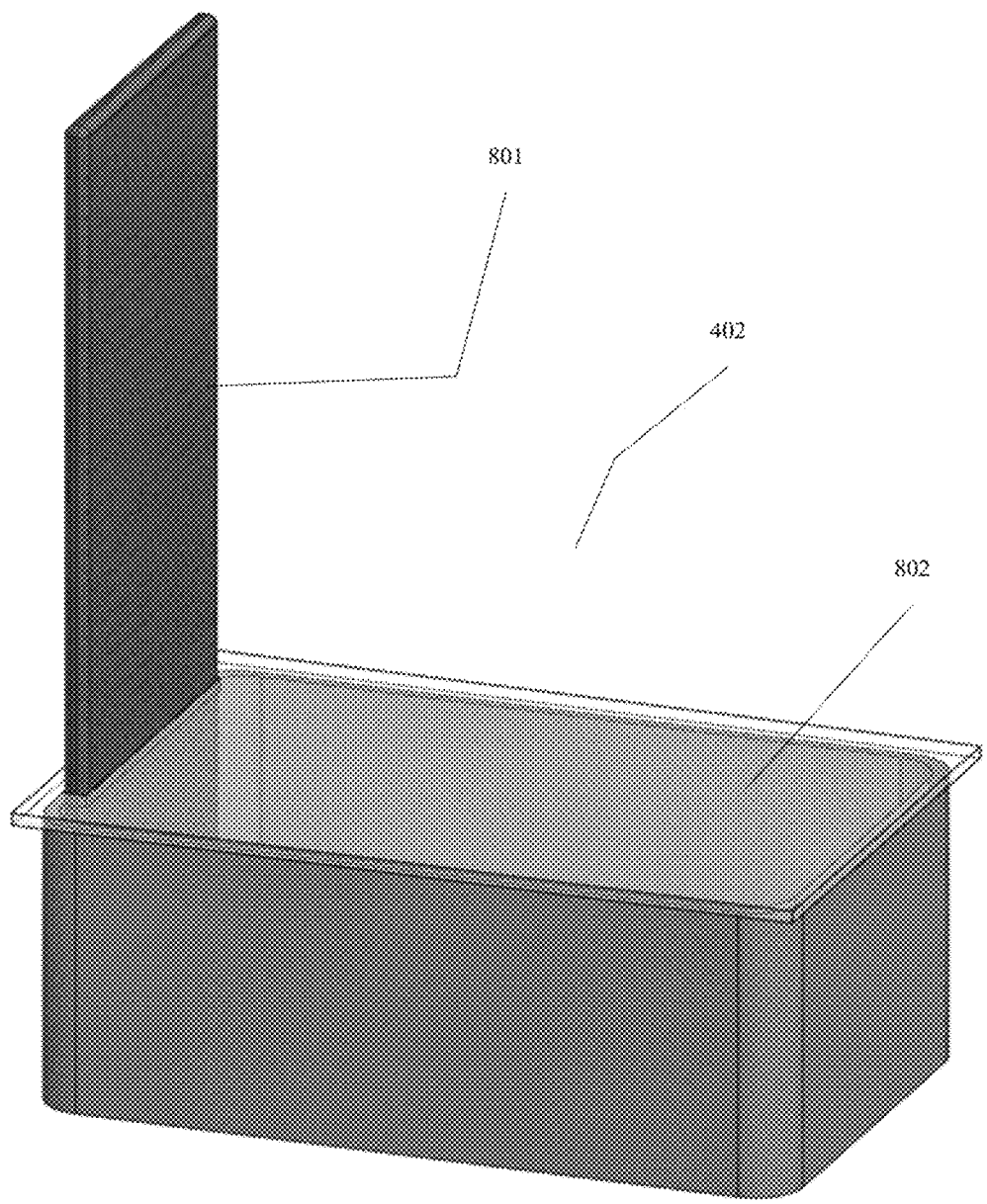
FIG. 7 which shows an Isometric View of the Fluid Delivery System.

Referring now to FIG. 7, which shows an Isometric View of the Fluid Delivery System (402).

The Fluid Delivery System Lid (802) serves the purpose of ensuring that the insects do not come in contact with too much of the fluid within the container at one time, thereby preventing the insects from drowning or becoming stuck in the fluid. The Fluid Delivery System Lid (802) may be solid or perforated. The Fluid Delivery System Lid (802) is required to keep the insects from coming in contact with too much of the liquid within the container at one time, thereby preventing the insects from drowning or becoming stuck in the liquid.

The Absorbent Material (801) is a moisture-wicking substrate which is capable of holding and obtaining water. The insects will be able to land directly onto the Absorbent Material (801) to obtain liquid for consumption or bathing.

Figure 8:
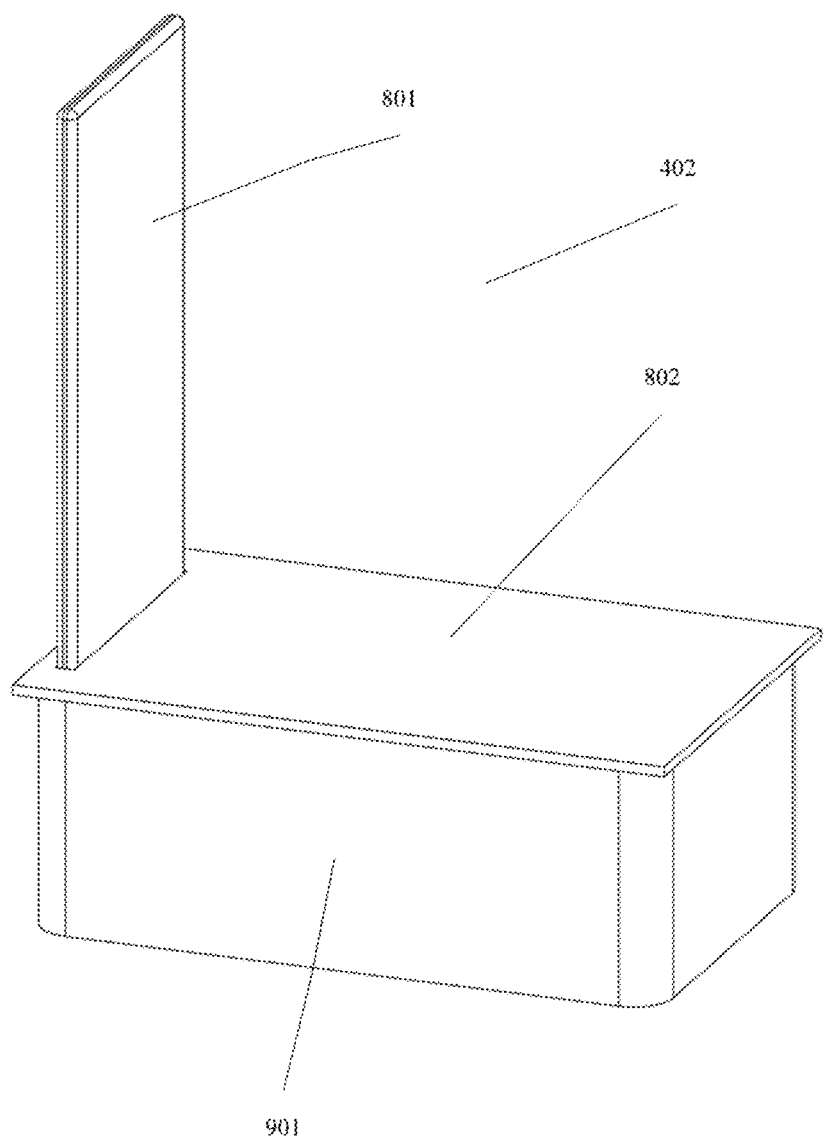
FIG. 8 which shows an Isometric View of the Fluid Delivery System.

Referring now to FIG. 8, which shows an Isometric View of the Fluid Delivery System (402).

The Impermeable Container (901) may be filled with various types of liquids for insect bathing and/or consumption. The liquid level must remain below the level of the Fluid Delivery System Lid (802) at all times while within the Breeding Module (101). The lid may be solid or perforated.

What is claimed is:

1. An apparatus for insect breeding and growth comprising:
   a. a breeding module wherein the breeding module further comprises:
      i. one or more fluid delivery systems, wherein said fluid delivery system is operably removeable and detached from the breeding module and further comprises a horizontal dimension and a vertical dimension, wherein one or more fluid delivery ports further comprise a height dimension and a width dimension wherein the horizontal and vertical dimensions of the fluid delivery system are slightly smaller than the height and width dimension of the fluid delivery port such that the fluid delivery system is capable of being inserted and removed through the fluid delivery port;
      ii. one or more walls, wherein said walls form an outer boundaries of the breeding module, and where each wall of said wall is connected to at least one other wall of said one or more walls, wherein one said wall is defined as a lid and the wall which directly opposes said lid is defined as a base wall and wherein one or more of said walls are each connected to form a shape which has an outside and an inside, wherein the outside of said shape is coterminous with the outside boundaries of said breeding module wherein said egg collection substrates are located and positioned on the inside of said shape and wherein the apparatus further comprises one or more insects wherein one or more insects are never located or found outside of said breeding module throughout the operation and use of said apparatus;
      iii. a breeding module moving enabler is operably attached to the base wall of the breeding module and is positioned on an axis which is perpendicular to both the lid and the breeding module moving enabler and further comprises:
         1. one or more access ports said access ports being apertures located fully within the breeding module moving enabler; and
      iv. one or more ports wherein said ports are apertures located on one or more of the walls of the breeding module; and
   b. one or more egg collection substrates;
   c. one or more light sources;
   d. one or more drainage ports;
   e. one or more cleaning ports;
   f. one or more access ports;
   g. one or more perforated ports wherein said perforated port comprises a screened material which is formed by a material comprised of one or more apertures of varying sizes and shapes which in concert allow for certain fluids or air or other objects to pass through said screened material while inhibiting objects that are larger than said apertures;
   h. one or more fluid delivery ports.

* * * * *